(12) United States Patent
Prammer

(10) Patent No.: US 6,204,663 B1
(45) Date of Patent: Mar. 20, 2001

(54) PULSE SEQUENCE AND METHOD FOR SUPPRESSION OF MAGNETO-ACOUSTIC ARTIFACTS IN NMR DATA

(75) Inventor: Manfred G Prammer, Downingtown, PA (US)

(73) Assignee: Numar Corporation, Malvern, PA (US)

( * ) Notice: Subject to any disclaimer, the term of this patent is extended or adjusted under 35 U.S.C. 154(b) by 0 days.

(21) Appl. No.: 08/826,132

(22) Filed: Mar. 26, 1997

(51) Int. Cl.$^7$ .................................................... G01V 3/00
(52) U.S. Cl. ............................................................ 324/303
(58) Field of Search .................................. 324/303, 300, 324/318, 322, 307, 309

(56) References Cited

U.S. PATENT DOCUMENTS

| | | | |
|---|---|---|---|
| 3,508,438 | 4/1970 | Alger et al. | 73/152 |
| 4,710,713 | 12/1987 | Taicher et al. | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,728,892 | 3/1988 | Vinegar et al. | 324/309 |
| 4,933,638 | 6/1990 | Kenyon et al. | 324/303 |
| 5,023,551 | 6/1991 | Kleinberg et al. | 324/303 |
| 5,212,447 | 5/1993 | Paltiel | 324/300 |
| 5,280,243 | 1/1994 | Miller | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,389,877 * | 2/1995 | Sezginer et al. | 324/303 |
| 5,412,320 | 5/1995 | Coates | 324/303 |
| 5,432,446 | 7/1995 | Macinnis et al. | 324/303 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,596,274 * | 1/1997 | Sezginer | 324/303 |
| 5,680,043 | 10/1997 | Hurlimann et al. | 324/303 |
| 5,698,979 * | 12/1997 | Taicher et al. | 324/303 |

FOREIGN PATENT DOCUMENTS

| | | | |
|---|---|---|---|
| 0 581 666 A3 | 2/1994 | (EP) | G01V/3/32 |
| 0 649 035 B1 | 4/1995 | (EP) | G01V/3/32 |

OTHER PUBLICATIONS

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

(List continued on next page.)

Primary Examiner—Louis Arana
(74) Attorney, Agent, or Firm—Pennie & Edmonds LLP

(57) ABSTRACT

Novel pulse sequence and data acquisition method are disclosed which eliminate the effects of spurious NMR signals caused by mechanical resonances within the measurement apparatus. The proposed method alleviates interference problems typically arising from strong "excitation" pulses in a sequence, and enables the use of the corresponding data points to increase the resolution of the measurement. The method is based on changing the measurement frequency between pulse sequences and averaging out data points obtained from the different sequences in a way that effectuates cancellation of the spurious signals. The novel cycle of ulse sequences and a data acquisition method can be used, or example, with any existing NMR logging instruments.

20 Claims, 6 Drawing Sheets

$$E_x - R_y - A - R_y - A - R_y - A - R_y - \text{etc.}$$

LEGEND:

$E_x$   EXCITATION PULSE WITH r.f. PHASE OF 0°
$R_y$   REFOCUSING PULSE WITH r.f. PHASE OF 90°
A     DATA SAMPLING AND ACQUISITION WINDOW
—     CONSTANT DELAY TIME $\tau$ (tau)

STANDARD CPMG NMR PULSE SEQUENCE

OTHER PUBLICATIONS

Carr et al., "Effects of Diffusion on Free Precision in Nuclear Magnetic Resonance Experiments," *Physical Review*, vol. 94. No. 3 (May 1, 1954), pp. 630–638.

*Schlumberger Wireline & Testing,* "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

Kleinberg et al., "Novel NMR Apparatus for Investigating an External Sample," *Journal of Magnetic Resonance,* (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," Society of Petroleum Engineers (1990), pp. 733–741.

Miller et al., "Spin Echo Magnetic Resonance Logging: Porosity and Free Fluid Index Determination," *Society of Petroleum Engineers* (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

*Schlumberger Technology News—Oilfield Bulletin,* "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs," SPWLA 35th Annual Logging Symposium (Jun. 26–29, 1995).

Prammer, M.G., "NMR Pore Size Distributions and Permeability at the Well Site,", *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Jackson et al., "Western Gas Sands Project Los Alamos NMR Well Logging Tool Development," Los Alamos National Laboratory (Oct. 1981–Sep. 1982), pp. 1–28.

Clavier et al., "The Theoretical and Experimental Bases for the 'Dual Water' Model for the Interpretation of Shaly Sands," *Journal of Petroleum Technology* (Apr. 1984), pp. 3–15.

Waxman et al., "Electrical Conductivities in Oil–Bearing Shaly Sands," *Society of Petroleum Engineers Journal* (1968) pp. 107–122.

* cited by examiner $$E_x - R_y - A - R_y - A - R_y - A - R_y - \text{etc.}$$

LEGEND:

- $E_x$     EXCITATION PULSE WITH r.f. PHASE OF 0°
- $R_y$     REFOCUSING PULSE WITH r.f. PHASE OF 90°
- A     DATA SAMPLING AND ACQUISITION WINDOW
- —     CONSTANT DELAY TIME $\tau$ (tau)

STANDARD CPMG NMR PULSE SEQUENCE

FIG.1

$$E_x - R_{-y} - A - R_{-y} - A - R_{-y} - A - R_{-y} - \text{etc.}$$

LEGEND:

- $E_x$     EXCITATION PULSE WITH r.f. PHASE OF 0°
- $R_{-y}$     REFOCUSING PULSE WITH r.f. PHASE OF −90°
- A     DATA SAMPLING AND ACQUISITION WINDOW
- —     CONSTANT DELAY TIME $\tau$ (tau)

PHASE-ALTERNATED CPMG NMR PULSE SEQUENCE

FIG.2

FREQ. 1: $E_x - R_y - A_{11} - R_y - A_{21} - R_y - A_{31} - R_y -$ etc.

FREQ. 2: $E_x - R_y - A_{12} - R_y - A_{22} - R_y - A_{32} - R_y -$ etc.

FREQ. 1: $E_x - R_{-y} - A_{13} - R_{-y} - A_{23} - R_{-y} - A_{33} - R_{-y} -$ etc.

FREQ. 2: $E_x - R_{-y} - A_{14} - R_{-y} - A_{24} - R_{-y} - A_{34} - R_{-y} -$ etc.

NEW MEASUREMENT CYCLE

FIG.3

PULSE SEQUENCE AND METHOD FOR SUPPRESSION OF MAGNETO-ACOUSTIC ARTIFACTS IN NMR DATA

FIELD OF THE INVENTION

The present invention concerns nuclear magnetic resonance (NMR) pulse sequences such as those used in evaluating earth formations. More specifically, the invention relates to pulse sequences and data acquisition methods which eliminate the effects of spurious signals caused by mechanical resonances within the measurement apparatus.

BACKGROUND OF THE INVENTION

Pulsed nuclear magnetic resonance (NMR) measurements alternate between transmitting high-powered radio-frequency (r.f.) pulses and receiving low-level response signals in a matter of a few ten or hundred microseconds. The combination of a strong static magnetic field and radio frequency pulses tend to excite mechanical resonances within the measurement apparatus, which resonances in turn cause an interference signal induced in the receiver system by a microphonic effect.

It has long been known that the interference arising from imperfect "refocusing" pulses can be canceled by repeating the measurement with the r.f. phase of the refocusing pulses inverted. This phase reversal does not affect the NMR signal, but inverts the phase of the interference. By acquiring both magnitude and phase of the compromised signals and by adding complex-valued measurements, the NMR signal is enhanced, while the "refocusing" interference is eliminated.

The above error cancellation scheme has become standard in practice, but it does not address interference problems arising from the "excitation" pulse, which typically is the first pulse in a long series of pulses. Changing the excitation phase would also change the phase of the NMR signal: excitation interference and NMR signal are always in phase with each other. Since often only the first data point ("echo") is affected by excitation interference, it is customary to eliminate this first data point from the data set. The first data point, however, contains valuable information about fast time-dependent behavior of the NMR sample and therefore having to ignore this point is an unsatisfactory solution.

The method of the present invention, described in more detail below, uses a novel cycle of pulse sequences to reduce the effect of "excitation" interference, on the basis of changing the measurement frequency between certain pulse sequences. Naturally, the method is especially useful for NMR measurements in which small changes in frequency can readily be allowed or tolerated. For example, laboratory-type NMR machines typically operate in homogeneous fields with a single, well-defined frequency. Changes in frequency are employed either to follow fluctuations in the main magnetic field, or to enable magnetic resonance imaging (MRI). NMR machines built for wireline logging or similar industrial applications are much more robust with respect to small changes in frequency. Therefore, the proposed solution is well-suited for industrial NMR applications.

The method of the present invention uses prior art NMR apparatuses and logging tools to obtain previously unavailable data relating to the fast time-dependent behavior of an NMR sample. In particular, a novel pulse sequence is proposed and used to obtain improved NMR data by eliminating spurious signals corresponding to mechanical resonances in the measurement apparatus induced by the r.f. excitation pulse.

SUMMARY OF THE INVENTION

Accordingly, it is an object of the present invention to provide a method for improving the accuracy of borehole NMR logging measurements.

It is another object of the present invention to provide a method for improving the short time resolution of borehole NMR logging measurements.

It is yet another object of the present invention to provide a method for suppressing of magneto-acoustic artifacts in NMR data obtained from logging measurements.

These and other objects are accomplished in accordance with a preferred embodiment of the present invention by a novel cycle of pulse sequences and a data acquisition scheme that employ existing NMR logging instruments. The novel cycle of pulse sequences of the present invention is characterized by a change in the measurement frequency between pulse sequences. In a preferred embodiment of the present invention, the frequency change is chosen so that spurious signals induced by the excitation pulse may be significantly reduced by combining NMR signals from corresponding echoes received in response to each measurement frequencies.

In accordance with the present invention, one can determine petrophysical properties of a geologic formation more accurately by reducing the effect of spurious signals arising from the excitation pulse. In particular, significant errors in the first spin-echo are corrected in accordance with a preferred embodiment of the present invention, which therefore provides increased short time resolution and allows improved detection and quantification of components which are associated with short relaxation times such as clay-bound water. In turn, this more accurate measurement of the clay-bound water improves determination of the total porosity and use of the resistivity interpretation model.

More specifically, in a preferred embodiment of the present invention an NMR method for measuring attributes of a material is disclosed, comprising the steps of: (a) applying at least one first pulse-echo sequence having an associated measurement frequency $F_1$; (b) applying at least one second pulse-echo sequence having an associated measurement frequency $F_2$ different from $F_1$; (c) measuring NMR signals corresponding to the first pulse-echo sequence and the second pulse-echo sequence, these NMR signals representing spin-echo relaxation in the material, at least some of the measured NMR signals being corrupted by spurious signals; (d) combining measured NMR signals from the first pulse-echo sequence and from the second pulse-echo sequence to reduce the effect of said spurious signals; and (e) determining properties of the material on the basis of the combination of measured signals.

In another preferred embodiment of the present invention which is directed to borehole logging, a method for NMR borehole logging is disclosed, comprising the steps of: (a) providing at least one first pulse-echo sequence associated with a first measurement frequency $F_1$; (b) providing at least one second pulse-echo sequence associated with a second measurement frequency $F_1$ different from $F_1$; (c) measuring NMR signals corresponding to the first pulse-echo sequence and the second pulse-echo sequence, the NMR signals representing spin-echo relaxation of a geologic formation in the borehole, at least some of the measured NMR signals being corrupted by spurious signals; (d) combining measured NMR signals from the first pulse-echo sequence and from the second pulse-echo sequence to reduce the effect of said spurious signals; and (e) determining properties of the geologic formation in the borehole on the basis of the combination of measured signals.

BRIEF DESCRIPTION OF THE DRAWINGS

For the purposes of understanding the principles underlying this invention, reference is now made to the drawings, in which:

FIG. 1 is an illustration of a standard pulse sequence employed by NMR logging tools.

FIG. 2 is an illustration of a phase-alternated version of the standard sequence shown in FIG. 1.

FIG. 3 illustrates the cycle of pulse sequences in accordance with a preferred embodiment of the present invention.

DETAILED DESCRIPTION OF THE PREFERRED EMBODIMENT

Figure 4A:
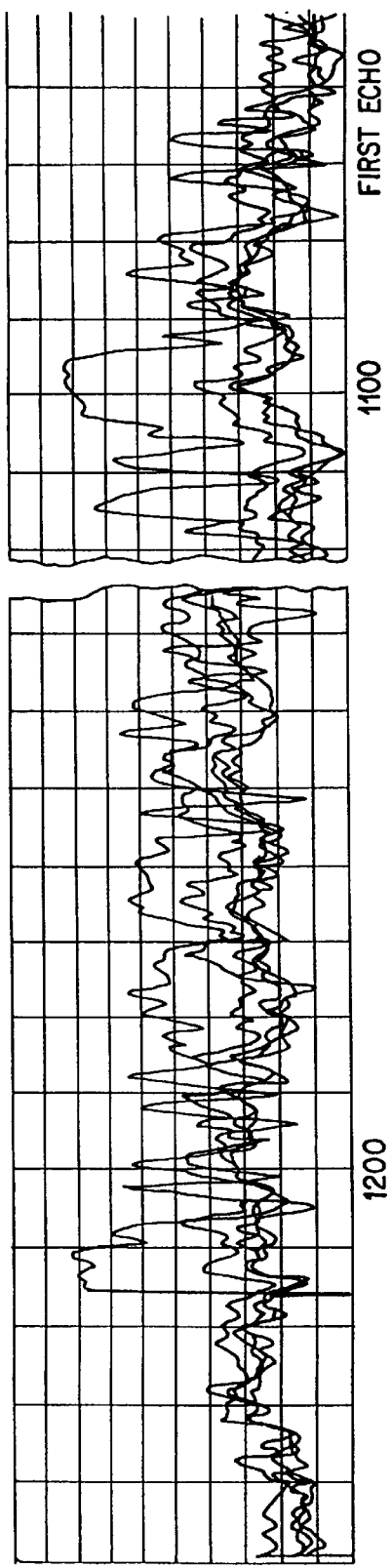
FIG. 4 is a standard field log illustrating curves from the first four data points from a phase-alternated CPMG sequence as a function of tool depth within a borehole.

The principles underlying this invention are described below with a more specific reference to an embodiment which is directed to improved NMR borehole logging methods.

There are two versions of modern pulse-NMR logging tools in use today: the centralized MRIL® tool made by NUMAR Corporation, and the side-wall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Millen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical conference of the SPE, New Orleans, La., Sep. 25–28, 1994). Details of the structure and the use of the MRIL® tool are also discussed in U.S. Pat. Nos. 4,717,876; 7,717,877; 4,717,878; 5,212,447; 5,280,243; 5,309,098; 5,412,320; 5,517,115 and 5,557,200, all of which are commonly owned by the assignee of the present invention.

The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992.

The content of the above patents and publications is hereby expressly incorporated by reference. It should be understood that the present invention is equally applicable to both hardware configurations discussed above.

With reference to the attached drawings, FIG. 1 shows a standard pulse sequence typically employed by NMR logging tools, such as the Numar MRIL® and the Schlumberger CMR tools. As shown in FIG. 1, an excitation pulse ($E_x$) with radio frequency (r.f.) phase of zero degrees is first applied. An echo train follows, with a wait time of τ(tau) between the excitation pulse and the first refocusing pulse, and between the refocusing pulses ($R_y$) and the acquisition windows (A). The phase-alternated version of the standard CPMG sequence is depicted in FIG. 2. This sequence is identical to the standard sequence, except that the refocusing pulses ($R_{-y}$) are 180 degrees out of phase, i.e., at a phase angle of minus 90 degrees with respect to the excitation pulse.

When the complex-valued NMR measurements acquired according to the standard and phase-alternated CPMG pulse sequences are added, the NMR signal is enhanced, and the interference arising from imperfect refocusing pulses is eliminated. This scheme does not however address problems associated with interference from the excitation pulse. In particular, the excitation pulse gives rise to microphonic interferences associated with mechanical resonances within the apparatus. These self-resonances occur within the measurement bandwidth but are not phase-locked to the NMR signal. These signals rather evolve with their intrinsic self-resonant frequency and exhibit a phase difference from the NMR signal that depends on the particular self-resonant frequency and the time delay between excitation and data acquisition. Typically, more than one self-resonance are located within the measurement bandwidth; their number and exact frequencies are in general unknown and also variable with time.

In accordance with a preferred embodiment of the present invention, a cycle of pulse sequences is applied, where the pulse sequences correspond to two or more frequencies. By alternating between at least two closely spaced NMR frequencies, the same resonances are excited. The phase difference between interference and NMR signal, however, evolves differently between excitation and data acquisition. Specifically, if the frequency change is made equal to one-half of the time between excitation pulse and acquisition, an additional phase difference of 180 degrees is induced.

The novel cycle of pulse sequences in accordance with a preferred embodiment of the present invention is shown in FIG. 3. The first pulse sequence in the cycle is identical to the one shown in FIG. 1, and the third pulse sequence is identical to the one shown in FIG. 2. The second and fourth pulse sequences are applied at a different frequency from the first and third pulse sequences. Acquisition windows $A_{ij}$ correspond to the ith echo in the jth pulse sequence. In a preferred embodiment, the frequency difference is a function of the time delay between excitation pulse and data acquisition:

$$|F_1 - F_2| = \frac{1}{(4\tau)}. \tag{1}$$

where $F_1$ is the frequency at which the first and third pulse sequences are applied, $F_2$ is the frequency at which the second and fourth pulse sequences are applied, and τ is the constant delay time both between the excitation pulse and the first refocusing pulse and between the refocusing pulses and the acquisition windows.

In a more general case, the frequency difference in Eqn. (1) can be expressed as:

$$|F_1 - F_2| \cong \left(n + \frac{1}{2}\right)\frac{1}{2\tau}, \tag{1A}$$

in which n is any integer or zero. It will be appreciated that for n=0, Eqn. (1A) is identical to Eqn. (1). However, generic Eqn. (1A) further indicates that due to the cyclic nature of the problem, a frequency difference corresponding to an additional offset of n/(2τ) will work also. Since keeping the frequency difference relatively small is desirable, however, it should be clear that the case in which n=0 is preferred.

Further, in accordance with a preferred embodiment of the present invention, data from all four measurements shown in FIG. 3 is added, which amplifies the NMR response and cancels both excitation and refocusing interference. In particular, data corresponding to the same acquisition slots are averaged using complex arithmetic:

$$A_1 = \tfrac{1}{4}(A_{11} + A_{12} + A_{13} + A_{14}), \quad (2A)$$

$$A_2 = \tfrac{1}{4}(A_{21} + A_{22} + A_{23} + A_{24}), \quad (2B)$$

$$A_3 = \tfrac{1}{4}(A_{31} + A_{32} + A_{33} + A_{34}), \quad (2C)$$

$$\ldots \text{etc.} \ldots, \quad (2D)$$

where averaged acquisition $A_k$ corresponds to the kth slot in each pulse sequence. Equation 2D indicates that this method can be used for an unlimited string of acquisition slots: as shown in FIG. 3, the refocusing pulses and corresponding acquisitions are repeated for the full length of the pulse sequence. Equation 2D, then, indicates that averaged acquisitions $A_k$ may be obtained for all acquisition slots k, in this example for slots k>3.

Measurement parameters which may be used in a preferred embodiment of the present invention are shown in the following Table of optimum frequency differences for different pulse spacings.

| $\tau$ | Evolution Time: ($2\tau$) | Frequency Difference: ($1/4\tau$) |
|---|---|---|
| 0.50 ms | 1.0 ms | 500 Hz |
| 0.25 ms | 0.5 ms | 1,000 Hz |

NMR machines typically operate at frequencies between 1 MHz and 100 MHz; therefore the frequency changes in the above table are on the order of 0.1% to 0.001% of the Larmor or measurement frequency.

Figure 5A:
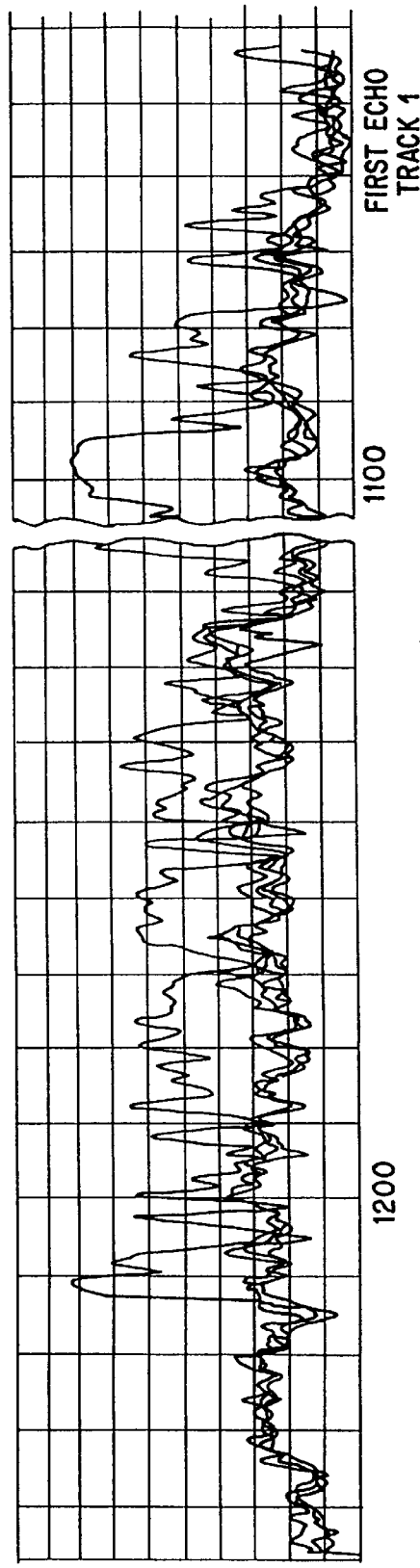
FIG. 5 illustrates the results of a field test of the novel cycle of pulse sequences and data acquisition method in accordance with a preferred embodiment of the present invention.
Figure 4B:
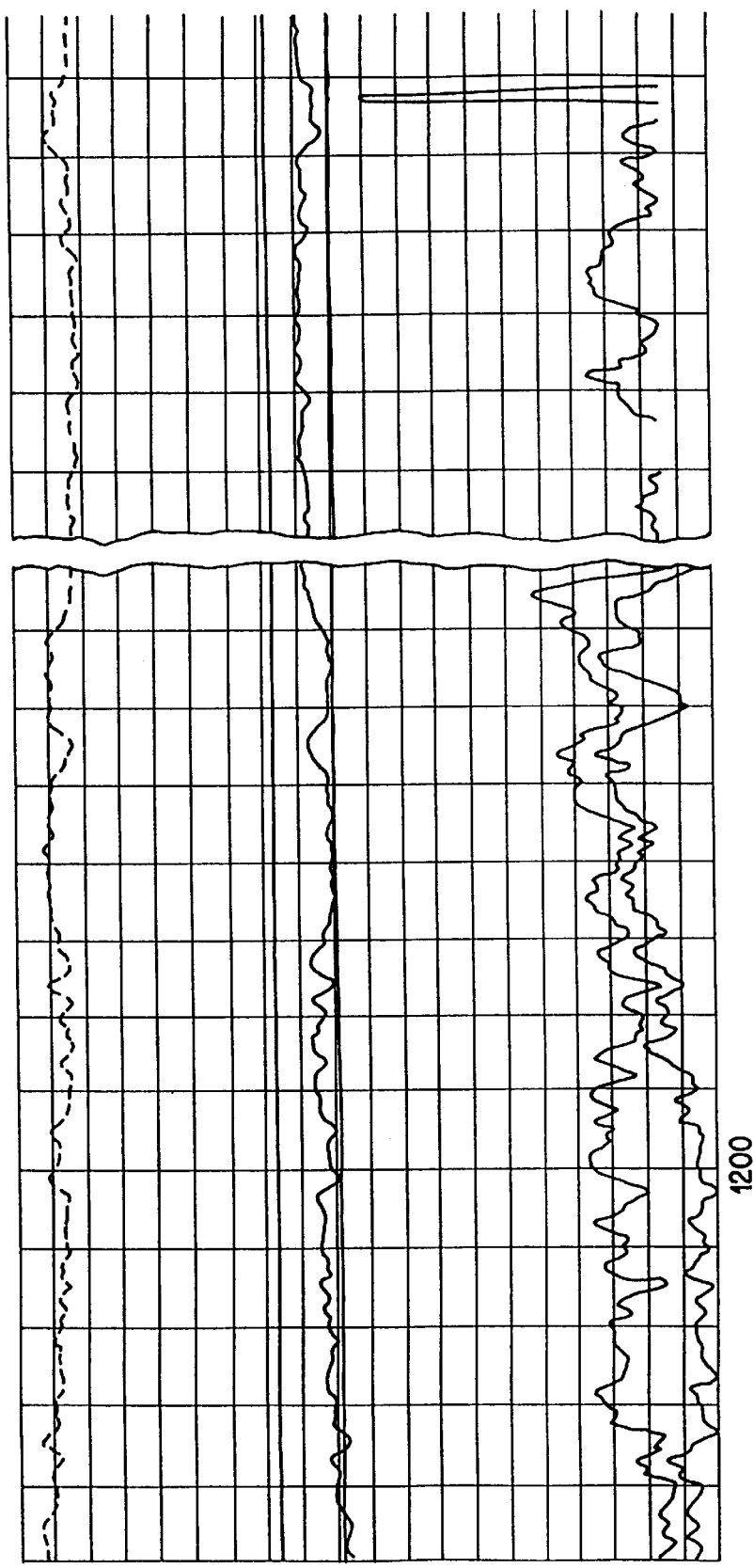
Figure 5B:
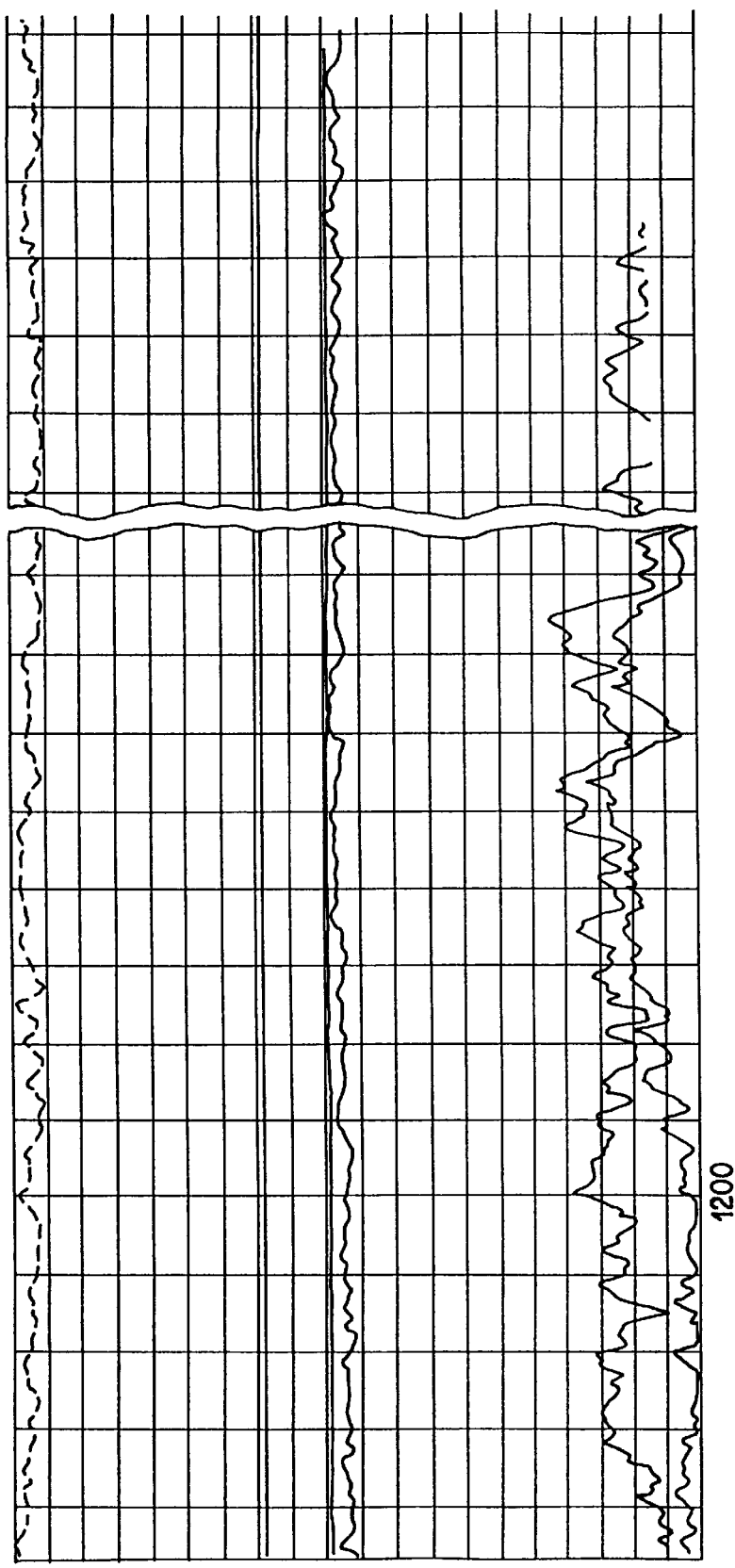

Results from field tests are illustrated in FIGS. 4 and 5. FIG. 4 is a standard field log which shows curves for the first four data points (echoes) from a phase-alternated CPMG sequence as a function of tool depth within the bore hole. Tool speed in this experiment was 5 ft/min, logging uphole. Every 3 seconds, the tool performed a CPMG pulse-echo sequence with 1,000 echoes and a pulse-to-pulse spacing of 0.51 msec. Four consecutive measurements were averaged. The operating frequency was 747 kHz. In this case, the first data point, marked as Track 1 in FIG. 4, is always abnormally high as a result of excitation interference.

FIG. 5 illustrates the results of a field test using the novel cycle of pulse sequences and data acquisition method of the present invention. The artifact which appears in FIG. 4 is corrected by invoking the frequency-cycling method of the present invention. For the measurement corresponding to FIG. 5, all parameters are were the same as that of FIG. 4, except that the operating frequency was alternated between 745 kHz and 746 kHz. Again, four consecutive measurements were averaged. Following the application of the ringing cancellation method of the present invention, the first data point, marked as Track 1 in FIG. 5, is shown to be correct.

Further results from field tests of the novel frequency-cycling method of the present invention are shown in Table 1. Data with pulse-to-pulse spacings ($2\tau$) of 0.51, 0.6 and 1.2 ms were acquired, both with and without the novel cycle of the present invention. The interference effect on the first data point without the present invention was a misreading ranging from −2 to +3 percent of full scale. With data around 10 percent of full scale, these are errors of −20% to +30%. When the novel frequency-cycling method of the present invention is used, the systematic data error is reduced to an insignificant amount.

TABLE 1

| Data Set | Frequencies | $2\tau$ | Comments |
|---|---|---|---|
| T1M | 747 kHz | 1.2 ms | first data points questionable |
| T1R | 747 kHz | 1.2 ms | first data points questionable |
| T1MAGM | 747.00/747.42 kHz | 1.2 ms | first data points clean |
| T1MAGR | 747.00/747.42 kHz | 1.2 ms | first data points clean |
| T2M | 745 kHz | 0.60 ms | first data points in error |
| T2R | 745 kHz | 0.60 ms | first data points in error |
| T2MAGM | 744.60/745.40 kHz | 0.60 ms | first data points clean |
| T2MAGR | 744.60/745.40 kHz | 0.60 ms | first data points clean |
| T3M | 747 kHz | 0.51 ms | first data points in error |
| T3R | 745 kHz | 0.51 ms | first data points in error |
| T3MAGM | 745/746 kHz | 0.51 ms | first data points clean |
| T3MAGR | 745/746 kHz | 0.51 ms | first data points clean |

Applications

The MRIL® tool is capable of performing a variety of borehole NMR logging measurements the accuracy of which can be improved using the method of the present invention. See, for example, co-pending U.S. patent application Ser. No. 08/822,567, filed Mar. 19, 1997, file wrapper continuation of U.S. application Ser. No. 08/542,340 assigned to the assignee of the present application, which teaches systems and methods for lithology independent gas detection. U.S. patent application Ser. No. 08/816,395, assigned to the assignee of the present application and which was filed Mar. 13, 1997 claiming priority of provisional application Ser. No. 60/013,484, teaches, among other things, the use of a rapid-fire CPMG pulse sequence to detect and quantify components having very short relaxation times, such as clay-bound water. The content of the above patent applications is hereby expressly incorporated by reference. These and other NMR measurement methods using the MRIL® tool, as well as measurement methods using the Schlumberger CMR tool, can be improved when performed in conjunction with the method of the present invention.

Figure 6:
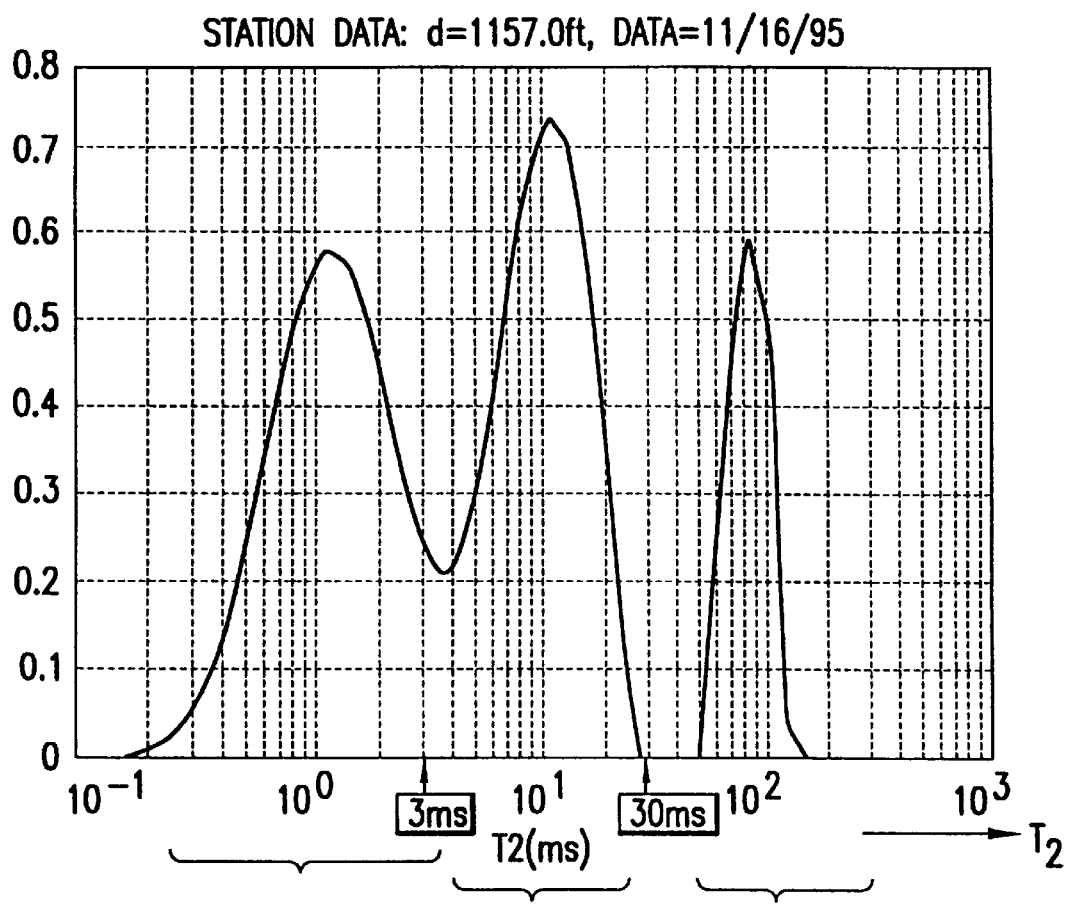
FIG. 6 illustrates the increased resolution which enables detection and measurement of the clay-bound water content in accordance with a preferred embodiment of the present invention.

In particular, as indicated above, the first echo in a CPMG echo train with echo spacing 0.51, 0.60 or 1.2 ms can be corrected using the method of the present invention. Data from the uncorrected echo trains is inaccurate for times shorter than 1.02, 1.2 or 2.4 ms, respectively because the first echo can not be used. The elimination of excitation interference clearly increases the spin-echo relaxation time resolution of the NMR measurement. For example, clay-bound water has spin-echo relaxation times on the order of 1 ms. Because of the corruption of the first data point, prior art methods were incapable of measuring relaxation signals of this order. As shown in FIG. 6, the increase in resolution using the method of the present invention enables one to not only detect but also measure the quantify of the clay-bound water component that is a contributing factor, for example, in total porosity measurements. This newly provided capability improves the utility and the accuracy of the measurements obtained using standard NMR tools.

Although the present invention has been described in connection with a preferred embodiment, it is not intended to be limited to the specific form set forth herein, but is intended to cover such modifications, alternatives, and equivalents as can reasonably be included within the spirit and scope of the invention as defined by the following claims.

What is claimed is:

1. An NMR method for measuring attributes of a material, comprising the steps of:
   a) applying at least one first pulse-echo sequence having an associated measurement frequency $F_1$;
   b) applying at least one second pulse-echo sequence having an associated measurement frequency $F_2$ different from $F_1$, the difference being a function of the time delay between excitation pulse and data acquisition for said first and second sequences;
   c) measuring NMR signals corresponding to said at least one first pulse-echo sequence and said at least one second pulse-echo sequence, said NMR signals representing spin-echo relaxation in the material, at least some of said measured NMR signals being corrupted by spurious signals;
   d) combining measured NMR signals from said at least one first pulse-echo sequence and from said at least one second pulse-echo sequence to reduce the effect of said spurious signals; and
   e) determining properties of the material on the basis of the combination of measured signals.

2. The method of claim 1 wherein said at least one first pulse-echo sequence and said at least one second pulse-echo sequence have an associated pulse echo spacing τ(tau); and wherein:

$$|F_1 - F_2| \cong \left(n + \frac{1}{2}\right)\frac{1}{2\tau},$$

in which n is any integer or zero.

3. The method of claim 2 wherein said at least one first pulse-echo sequence and said at least one second pulse-echo sequence are Carr-Purcell-Meiboom-Gill (CPMG) sequences.

4. The method of claim 3 wherein:
   said at least one first CPMG pulse sequence comprises two or more first CPMG pulse sequences,
   at least one of said two or more first CPMG pulse sequences having refocusing pulses which are 180 degrees out of phase with the refocusing pulses of any other pulse sequence of said two or more first CPMG pulse sequences; and
   said at least one second CPMG pulse sequence comprises two or more second CPMG pulse sequences;
   at least one of said two or more second CPMG pulse sequences having refocusing pulses which are 180 degrees out of phase with the refocusing pulses of any other pulse sequence of said two or more second CPMG pulse sequences;
   and the step of combining comprises the step of:
      combining corresponding echo signals from said two or more first CPMG pulse sequences and said two or more second CPMG pulse sequences to reduce the effect on said NMR signals of imperfect refocusing pulses.

5. The method of claim 1 wherein the property of the material being determined is its porosity.

6. The method of claim 1 wherein the spurious signals the effect of which is reduced are magneto-acoustic signals.

7. A method for NMR borehole logging comprising the steps of:
   a) providing at least one first pulse-echo sequence associated with a first measurement frequency $F_1$;
   b) providing at least one second pulse-echo sequence associated with a second measurement frequency $F_2$ different from $F_1$, the difference being a function of the time delay between excitation pulse and data acquisition for said first and second sequences;
   c) measuring NMR signals corresponding to said at least one first pulse-echo sequence and said at least one second pulse-echo sequence, said NMR signals representing spin-echo relaxation of a geologic formation in the borehole, at least some of said measured NMR signals being corrupted by spurious signals;
   d) combining measured NMR signals from said at least one first pulse-echo sequence and from said at least one second pulse-echo sequence to reduce the effect of said spurious signals; and
   e) determining properties of the geologic formation in the borehole on the basis of the combination of measured signals.

8. The method of claim 7 wherein said at least one first pulse-echo sequence and said at least one second pulse-echo sequence have an associated pulse echo spacing τ(tau); and wherein:

$$|F_1 - F_2| \cong \left(n + \frac{1}{2}\right)\frac{1}{2\tau},$$

in which n is any integer or zero.

9. The method of claim 8 wherein said at least one first pulse-echo sequence and said at least one second pulse-echo sequence are Carr-Purcell-Meiboom-Gill (CPMG) sequences.

10. The method of claim 9 wherein:
    said at least one first CPMG pulse sequence comprises two or more first CPMG pulse sequences,
    at least one of said two or more first CPMG pulse sequences having refocusing pulses which are 180 degrees out of phase with the refocusing pulses of any other pulse sequence of said two or more first CPMG pulse sequences; and
    said at least one second CPMG pulse sequence comprises two or more second CPMG pulse sequences;
    at least one of said two or more second CPMG pulse sequences having refocusing pulses which are 180 degrees out of phase with the refocusing pulses of any other pulse sequence of said two or more second CPMG pulse sequences;
    and the step of combining comprises the step of:
       combining corresponding echo signals from said two or more first CPMG pulse sequences and said two or more second CPMG pulse sequences to reduce the effect on said NMR signals of imperfect refocusing pulses.

11. The method of claim 7 wherein the spurious signals the effect of which is reduced are magneto-acoustic signals.

12. The method of claim 7 wherein the property of the material being determined is its porosity.

13. The method of claim 7 wherein the step of determining comprises the step of providing information about components of the geologic formation in the borehole which have very fast relaxation times.

14. A method for NMR borehole logging comprising the steps of:
    a) providing at least one first pulse-echo sequence associated with a first measurement frequency $F_1$;
    b) providing at least one second pulse-echo sequence associated with a second measurement frequency $F_2$ different from $F_1$, wherein said at least one first pulse-echo sequence and said at least one second pulse-echo sequence have an associated pulse echo spacing τ such that:

$$|F_1 - F_2| \cong \left(n + \frac{1}{2}\right)\frac{1}{2\tau};$$

in which n is any integer or zero;

c) receiving NMR signals in response to said at least one first and said at least one second pulse-echo sequences; and d) determining properties of a geologic formation in the borehole on the basis of the received NMR signals.

15. The method of claim 14 wherein said at least one first pulse-echo sequence and said at least one second pulse-echo sequence are Carr-Purcell-Meiboom-Gill (CPMG) sequences.

16. The method of claim 15 wherein:

said at least one first CPMG pulse sequence comprises two or more first CPMG pulse sequences, at least one of said two or more first CPMG pulse sequences having refocusing pulses which are 180 degrees out of phase with the refocusing pulses of any other pulse sequence of said two or more first CPMG pulse sequences; and said at least one second CPMG pulse sequence comprises two or more second CPMG pulse sequences;

at least one of said two or more second CPMG pulse sequences having refocusing pulses which are 180 degrees out of phase with the refocusing pulses of any other pulse sequence of said two or more second CPMG pulse sequences;

and the step of combining comprises the step of:

combining corresponding echo signals from said two or more first CPMG pulse sequences and said two or more second CPMG pulse sequences to reduce the effect on said NMR signals of imperfect refocusing pulses.

17. The method of claim 14 wherein the property of the geologic formation being determined is its porosity.

18. The method of claim 14 wherein the step of determining comprises the step of providing information about components of the geologic formation in the borehole which have very fast relaxation times.

19. A method for NMR borehole logging, comprising:

(a) producing a static magnetic field into the volume of the formation substantially surrounding a borehole;

(b) producing a cycle of CPMG pulse sequences according to the expression:

(1)$F_1$: $E_x$ (-$R_y$-$A_{i1}$)$_i$ i≧1
(2)$F_2$: $E_x$ (-$R_y$-$A_{i2}$)$_i$ i≧1
(3)$F_1$: $E_x$ (-$R_{-y}$-$A_{i3}$)$_i$ i≧1
(4)$F_2$: $E_x$ (-$R_{-y}$-$A_{i4}$)$_i$ i≧1 where the first (1) and third (3) pulse sequences use measurement frequency $F_1$; the second (2) and fourth (4) pulse sequences use measurement frequency $F_2$;

$E_x$ is an excitation pulse with R.F. phase of 0°;

$R_{\pm y}$ designates a refocusing pulse with R.F. phase equal to ±90°;

$A_{ij}$ designates an acquisition window for the ith echo in the jth pulse sequence (j=1, 2, 3, 4); and —is a constant delay time τ;

(c) combining data acquired from the four pulse sequences in (b) as to cancel excitation and refocusing interference signals; and (d) determining properties of the formation substantially surrounding the borehole based on the combined data.

20. The method of claim 19 wherein the step of combining comprises averaging complex input data corresponding to the same acquisition echo, such that $DA_k = \frac{1}{4}(DA_{k1} + DA_{k2} + DA_{k3} + DA_{k4})$; k≧1 where averaged data acquisition $DA_k$ corresponds to data $DA_{kj}$ acquired in the $A_{kj}$ acquisition window.

* * * * *